(12) United States Patent
Kang et al.

(10) Patent No.: US 10,780,187 B2
(45) Date of Patent: Sep. 22, 2020

(54) APPARATUS AND METHOD FOR STERILIZING INTERNAL CHANNEL SURFACE OF ENDOSCOPE

(71) Applicant: PUKYONG NATIONAL UNIVERSITY INDUSTRY-UNIVERSITY COOPERATION FOUNDATION, Busan (KR)

(72) Inventors: Hyun Wook Kang, Busan (KR); Don Haeng Lee, Seoul (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 245 days.

(21) Appl. No.: 15/842,651

(22) Filed: Dec. 14, 2017

(65) Prior Publication Data
US 2019/0038789 A1 Feb. 7, 2019

(30) Foreign Application Priority Data
Aug. 7, 2017 (KR) .................. 10-2017-0099724

(51) Int. Cl.
| | | |
|---|---|---|
| A61L 2/10 | (2006.01) | |
| A61L 2/08 | (2006.01) | |
| A61L 2/16 | (2006.01) | |
| A61B 1/12 | (2006.01) | |
| A61L 2/18 | (2006.01) | |
| A61B 90/70 | (2016.01) | |

(52) U.S. Cl.
CPC ............... *A61L 2/10* (2013.01); *A61B 1/122* (2013.01); *A61B 1/125* (2013.01); *A61B 90/70* (2016.02); *A61L 2/085* (2013.01); *A61L 2/16* (2013.01); *A61L 2/186* (2013.01); *A61B 2090/701* (2016.02); *A61L 2202/14* (2013.01); *A61L 2202/24* (2013.01)

(58) Field of Classification Search
CPC ............... A61L 2/10; A61L 2/085; A61L 2/20
See application file for complete search history.

(56) References Cited

U.S. PATENT DOCUMENTS

| | | | | |
|---|---|---|---|---|
| 2003/0213074 A1* | 11/2003 | Kawazoe | ............... | A61B 1/122 15/3.5 |
| 2017/0182194 A1* | 6/2017 | Shin | ...................... | A61B 1/121 |

FOREIGN PATENT DOCUMENTS

| | | |
|---|---|---|
| KR | 10-2007-0046769 A | 5/2007 |
| KR | 10-2013-0000043 A | 1/2013 |
| KR | 10-2014-0096951 A | 8/2014 |
| KR | 10-1644072 B1 | 8/2016 |

* cited by examiner

*Primary Examiner* — Donald R Spamer

(57) ABSTRACT

Provided are an apparatus and method for sterilizing an internal channel surface of an endoscope, and more particularly, to an apparatus and method for sterilizing an internal channel surface of an endoscope, in which ultrasonic and infrared rays are irradiated to an internal channel of the endoscope to partially or entirely sterilize and removing a biofilm generated on the internal channel surface of the endoscope during a procedure or diagnosis.

12 Claims, 8 Drawing Sheets

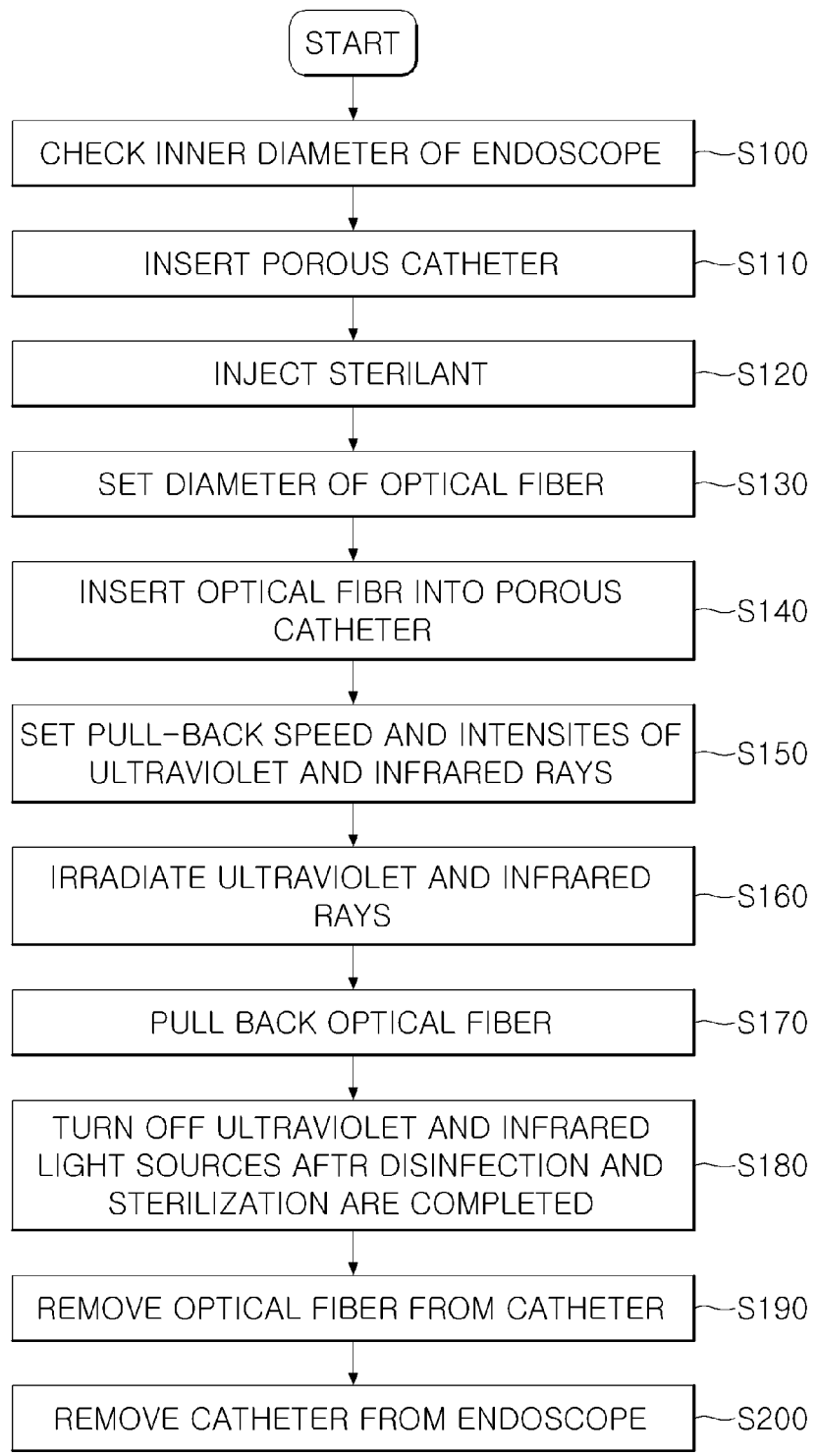

APPARATUS AND METHOD FOR STERILIZING INTERNAL CHANNEL SURFACE OF ENDOSCOPE

RELATED APPLICATION

This application claims the benefit of Korean Patent Application No. 10-2017-0099724, filed on Aug. 7, 2017, in the Korean Intellectual Property Office, the disclosure of which is incorporated herein in its entirety by reference.

BACKGROUND OF THE INVENTION

1. Field of the Invention

The present invention relates to an apparatus and method for sterilizing an internal channel surface of an endoscope, and more particularly, to an apparatus and method for sterilizing an internal channel surface of an endoscope, in which ultrasonic and infrared rays are irradiated to an internal channel of the endoscope to partially or entirely sterilize and removing a biofilm generated on the internal channel surface of the endoscope during a procedure or diagnosis.

2. Description of the Related Art

In recent years, reach has been conducted into a method that is harmless to the human body and is capable of effectively sterilizing pathogens in cleaning of reusable medical devices such as a catheter, a trocar, a surgical instrument, and the like, which are inserted into an endoscope device, which is inserted into organs of the human body for examination, or a blood vessel.

In general, reusable medical devices or patient care facilities are sterilized prior to each use and then inserted into the human tissues or blood vessels.

Typically, there are a method for disinfecting medical devices by aerosolizing hot steam and a method for disinfecting medical device by airing an ethylene oxide gas or performing thermal drying as disinfecting and sterilizing methods that are performed in the hospitals.

However, the above methods have limitations in which the methods are difficult to be applied to sterilization and disinfection of heat-sensitive medical devices. As a result, although the method for sterilizing and disinfecting the heat-sensitive medical devices by directly treating or diluting chemicals is performed, there is a limitation in which the chemicals not only have a bad influence on the human body in spite of sterilizing pathogenic bacteria, but also have an insufficient sterilization state.

Furthermore, in case of the endoscope, the biofilm generated in the endoscope is not effectively removed because of its structural characteristics.

PRIOR ART DOCUMENT

Patent Document

Korean Patent Publication No. 10-2013-0000043
Korean Patent Publication No. 10-2007-0046769
Korean Patent Publication No. 10-2014-0096951
Korean Patent Registration No. 10-1644072

SUMMARY OF THE INVENTION

One or more embodiments of the present invention include an apparatus and method for sterilizing an internal channel surface of an endoscope, in which ultrasonic and infrared rays are irradiated to an internal channel of the endoscope by using an optical fiber to partially or entirely sterilize and removing a biofilm generated on the internal channel surface of the endoscope during a procedure or diagnosis.

According to one or more embodiments of the present invention, an apparatus for sterilizing an internal channel surface of an endoscope includes: an ultraviolet light source configured to irradiate ultraviolet rays; an infrared light source configured to irradiate infrared rays; a porous catheter inserted into the endoscope; an optical fiber disposed in the porous catheter to irradiate the ultraviolet rays and the infrared rays to a surface of the inside of the endoscope; a coupling part configured to couple the ultraviolet rays and the infrared rays, which are respectively emitted from the ultraviolet light source and the infrared light source, to each other and thereby to output the coupled rays to the optical fiber; a pull-back driver configured to provide pull-back of the optical fiber; an injection device configured to inject a sterilant into the endoscope through the porous catheter; and an injection tubing configured to connect the injection device to the porous catheter.

The ultraviolet light source may use a wavelength of about 390 nm to about 490 nm and have a light output range of about 10 mW to about 5 W.

The ultraviolet light source may include one of a diode laser, a frequency multiplied solid state laser, an UV flash lamp, and a light emitting diode (LED).

The infrared light source may use a frequency of about 700 nm to about 2,000 nm and have a light output range of about 10 mW to about 10 W.

The infrared light source may include one of a diode laser, a frequency multiplied solid state laser, an IR flash lamp, a light emitting diode (LED), and an infrared bulb.

The apparatus may further include a centring wire disposed at an irradiation portion of an end of the optical fiber to locate the optical fiber at a center of the endoscope.

The centring wire may be made of a shape-memory material.

The porous catheter may include an optical fiber channel and a sterilant channel therein, and each of the optical fiber channel and the sterilant channel may have a circular cross-section, the optical fiber channel and the sterilant channel may be installed in parallel to each other, and the optical fiber channel may have a diameter greater than that of the sterilant channel.

The porous catheter may include an optical fiber channel and a sterilant channel therein, and the optical fiber channel may have a circular cross-section, and the sterilant channel may be disposed in a separated half-moon shape around the optical fiber channel.

An end of the optical fiber may include one of a cylindrical type diffusion part, a linear type diffusion part, a lateral type diffusion part, a hemispherical type diffusion part, or a partial cylindrical type diffusion part.

The apparatus may further include a protection cap disposed on an end of the optical fiber to protect the end of the optical fiber.

According to one or more embodiments of the present invention, a method for sterilizing an internal channel surface of an endoscope includes: (A) checking an inner diameter of the endoscope to insert a porous catheter according to a size of the checked inner diameter of the endoscope into the endoscope; (B) injecting a sterilant into the porous catheter to inject the sterilant into the endoscope; (C) inserting an optical fiber into the porous catheter to irradiate ultraviolet and infrared rays and thereby to pull back the optical fiber; and (D) removing the optical fiber after turning off an ultraviolet light source and an infrared light source to remove the porous catheter from the inside of the endoscope.

(C) The inserting of the optical fiber into the porous catheter may include: (C-1) setting a diameter of the optical fiber to insert the optical fiber into the porous catheter; (C-2) setting a pull-back speed of the optical fiber and intensities of the ultraviolet and infrared rays; (C-3) irradiating the ultraviolet and infrared rays; and (C-4) pulling back the optical fiber.

(D) The removing of the optical fiber may include: (D-1) turning off the ultraviolet light source and the infrared light source when the sterilization of the internal channel surface of the endoscope is completed; (D-2) removing the optical fiber from the porous catheter; and (D-3) removing the porous catheter from the endoscope.

BRIEF DESCRIPTION OF THE DRAWINGS

The above and other objects, features and other advantages of the present invention will be more clearly understood from the following detailed description taken in conjunction with the accompanying drawings, in which:

FIG. 7 is a flowchart of a method for sterilizing an internal channel surface of an endoscope according to an embodiment of the present invention.

DESCRIPTION OF THE PREFERRED EMBODIMENTS

Since the present invention may have diverse modified embodiments, exemplary embodiments will be described in detail with reference to the accompanying drawings.

The following embodiments are provided to help comprehensive understanding of a method, an apparatus, and/or a system described in the present specification. However, this is merely an example, and the present invention is not limited thereto.

In descriptions of embodiments of the present invention, detailed descriptions related to the well-known technologies will be ruled out in order not to unnecessarily obscure subject matters of the present invention. Also, terms used in the present specification are terms defined in consideration of functions according to embodiments, and thus the terms may be changed according to the intension or usage of a user or operator. Therefore, the terms should be defined on the basis of the overall contents of this specification. The terms used in the present specification are merely used to describe particular embodiments, and are not intended to limit the present invention. An expression used in the singular encompasses the expression in the plural, unless it has a clearly different meaning in the context. In the present specification, it is to be understood that tams such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Also, it will be understood that although the terms "first" and "second" are used herein to describe various elements, these elements should not be limited by these terms. The terms are only used to distinguish one component from another.

Figure 1:
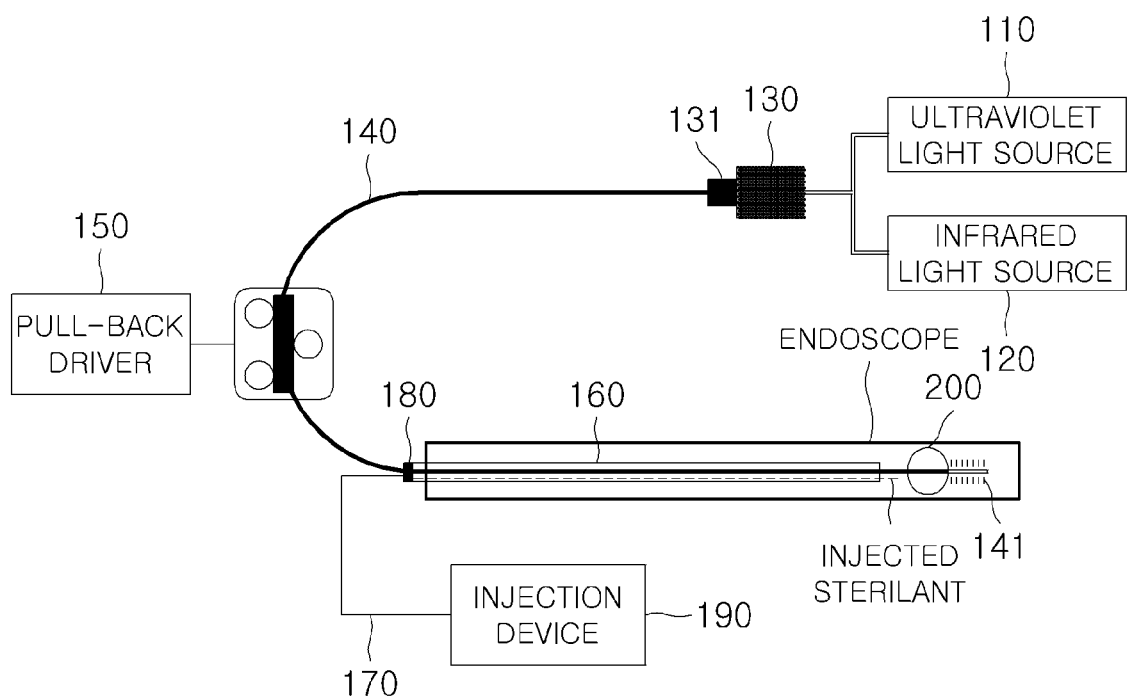
FIG. 1 is a view of an apparatus for sterilizing an internal channel surface of an endoscope according to an embodiment of the present invention.

FIG. 1 is a view of an apparatus for sterilizing an internal channel surface of an endoscope according to an embodiment of the present invention.

Referring to FIG. 1, an apparatus for sterilizing an internal channel surface of an endoscope according to an embodiment of the present invention includes an ultraviolet (UV) light source 110, an infrared (IR) light source 120, a coupling part 130, an optical fiber 140, a pull-back driver 150, a porous catheter 160, an injection tubing 170, a connection fixing part 180, an injection device 190, and a centring wire 200.

In the above-described constituents, the UV light source 110 uses a wavelength of about 390 nm to about 490 nm and has a light output range of about 10 mW to about 5 W.

The UV light source 110 includes a diode laser, a frequency multiplied solid state laser, an UV flash lamp, a light emitting diode (LED), and the like.

The IR light source 120 uses a frequency of about 700 nm to about 2,000 nm and has a light output range of about 10 mW to about 10 W.

The IR light source 120 includes a diode laser, a frequency multiplied solid state laser, an IR flash lamp, a light emitting diode (LED), an infrared bulb, and the like.

A method used when the UV light source 110 emits light having an UV wavelength is performed in a continuous wave or pulsed mode.

Also, a method used when the IR light source 120 emits light having an IR wavelength is performed in a continuous wave or pulsed mode.

Here, a pulse used in the pulsed mode has a length ranging from nanoseconds (ns) to milliseconds (ms) and a repetition rate of about 10 Hz to about 10 kHz.

The UV light source 110 and the IR light source 120 starts the sterilization of the internal channel by using the optical fiber 140 after an output is previously set before sterilizing the internal channel of the endoscope.

Figure 2:
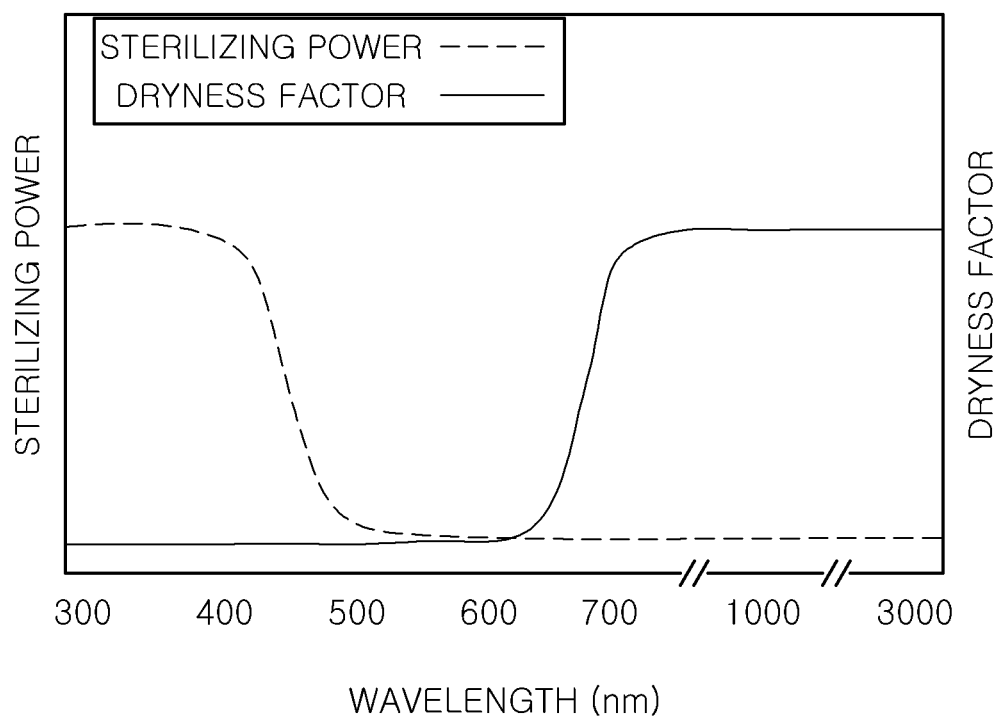
FIG. 2 is a graph illustrating a variation in sterilizing power and a dryness factor according to a wavelength.

A biofilm generated on the internal surface of the endoscope consists of viruses, bacteria, proteins, polysaccharides, pathogens, and the like. As illustrated in FIG. 2, a disinfection effect differs depending on the wavelength to be irradiated.

Particularly, in the sterilization of the internal channel of the endoscope, the UV wavelength is used to sterilize the bacteria, the proteins, the polysaccharides, the pathogens, and the like within the biofilm. In the sterilization of the internal channel of the endoscope, the IR wavelength is used to dry the biofilm at a low temperature of about 40° C. to about 70° C. and thereby to improve the sterilization and resolve the proteins.

UV rays and IR rays, which are respectively emitted from the UV light source 110 and the IR light source 120 may be adequately controlled by adjusting a kind of optical fiber, a pull-back speed of the optical fiber, a distance between the optical fiber and the surface of the endoscope, an inner diameter of the endoscope, and the like so that the internal channel surface of the endoscope is not damaged.

The coupling part 130 couples the UV rays emitted from the UV light source 110 to the IR rays emitted from the IR light source 120 to output the coupled rays.

As described above, the coupling part 130 may transmit the wavelengths of the UV rays and the IR rays to the internal channel surface of the endoscope at the same time to sterilize the internal channel of the endoscope.

Alternatively, the UV light source 110 and the IR light source 120 may be driven at different times to sequentially transmit the wavelengths of the UV rays and the IR rays to the internal channel surface of the endoscope.

As described above, the coupling part 130 may couple the UV rays to the IR rays by using a beam splitter and integrate energy to the connected optical fiber 140 by using an optical lens to transmit the integrated energy.

The coupling part 130 includes a connector 131 for connecting the optical fiber 140.

The optical fiber 140 may transmit the wavelengths of the UV rays and the IR rays to the internal channel of the endoscope and may be made of low/high OH silica, fused silica, germanium oxide, fluoride, phosphate, chalcogenide, hollow wave guide materials, or the like.

The optical fiber 140 is constituted by a core, a cladding, a buffer, and a jacket. The core of the optical fiber may have a diameter of about 0.2 mm to about 1 mm according to a density of the transmitted energy. The optical fiber may have a total diameter of about 0.4 mm to about 1.3 mm according to an inner diameter of the endoscope and a total length of about 1 m to about 4 m according to a length of the endoscope.

The optical fiber 140 may pass through the pull-back driver 150 and then be inserted into the endoscope to sterilize the internal channel surface of the endoscope. The pull-back driver 150 moves the optical fiber 140 forward and backward when the UV rays/IR rays are irradiated.

The optical fiber 140 provided in the pull-back driver 150 has a pull-back speed of about 0.5 mm/s to about 30 mm/s according to whether the sterilant is used together and a thickness of the biofilm.

Figure 3A:
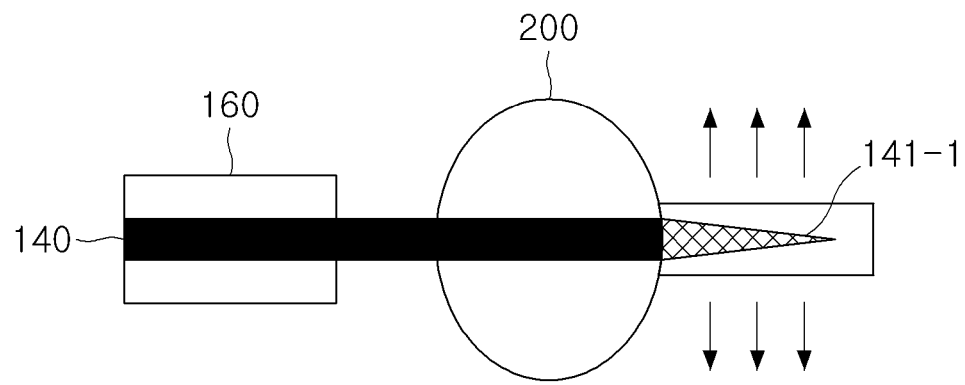
FIG. 3A is a view of a cylindrical type diffusion part.
Figure 3B:
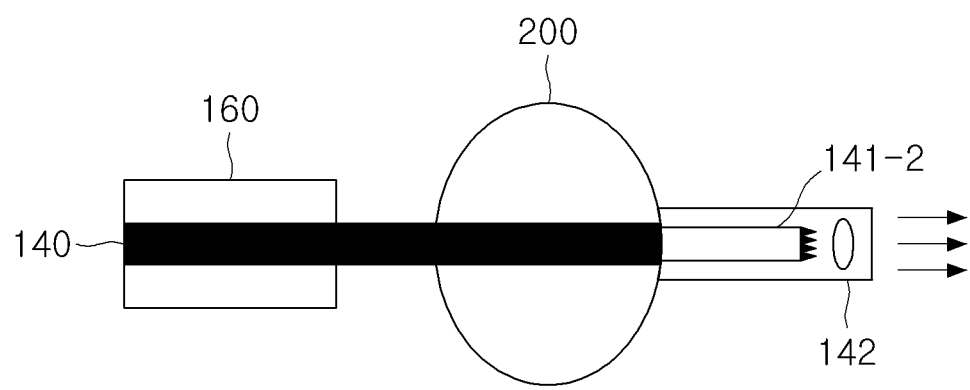
FIG. 3B is a view of a linear type diffusion part.
Figure 3C:
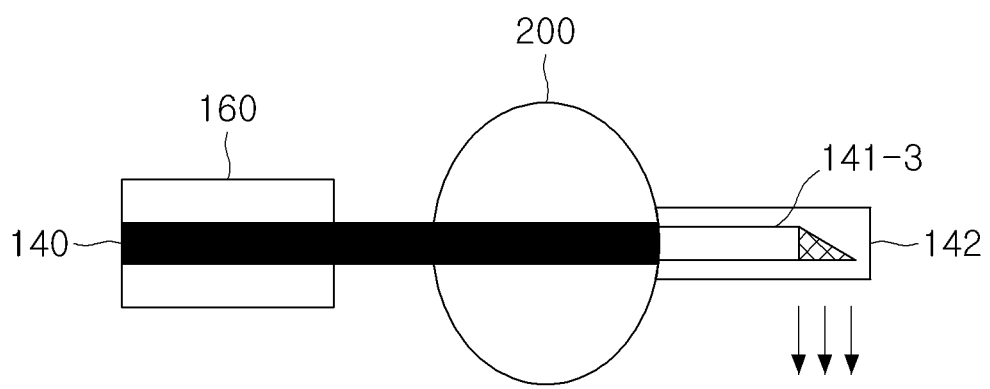
FIG. 3C is a lateral type diffusion part.
Figure 3D:
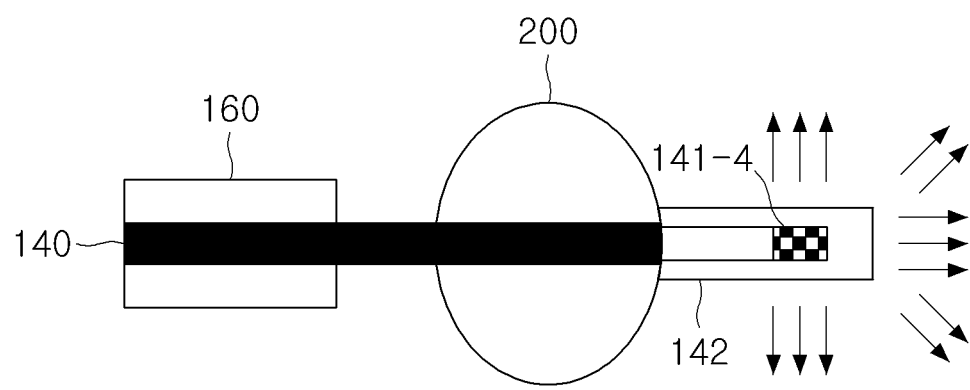
FIG. 3D is a hemispherical type diffusion part.
Figure 3E:
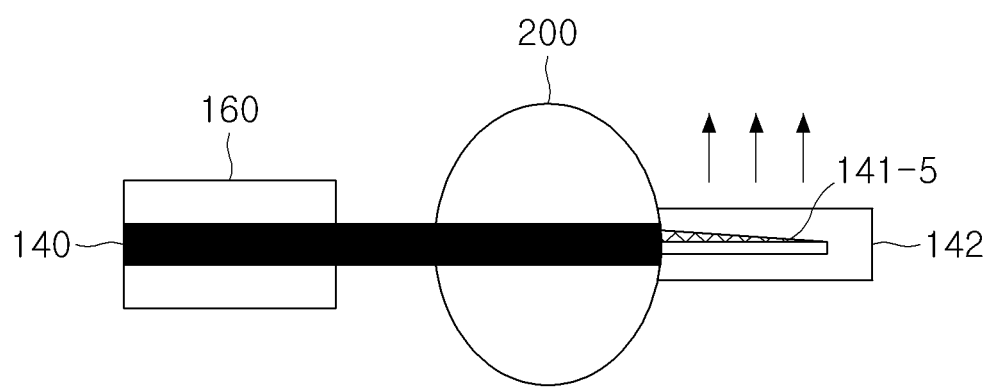
FIG. 3E is a partial cylindrical type diffusion part.

The light source energy may be transmitted from an end of the optical fiber 140 to sterilize the internal channel surface of the endoscope. Here, the light energy may be transmitted in a direction that is determined by a cylindrical type diffusion part 141-1 of FIG. 3A, a linear type diffusion part 141-2 of FIG. 3B, a lateral type diffusion part 141-3 of FIG. 3C, a hemispherical type diffusion part 141-4 of FIG. 3D, or a partial cylindrical type diffusion part 141-5 of FIG. 3E according to processed shapes of the end of the optical fiber 140.

In case of the cylindrical type or partial cylindrical type diffusion part, the end of the optical fiber may be etched to be tapered, and then, the etched surface may be processed to form a pattern so that light is transmitted to the cylindrical portion or the partial cylindrical portion.

To irradiate laser through the cylindrical or partial cylindrical type diffusion part, the end of the optical fiber 140 may be processed to have a length of about 0.5 cm to about 5 cm according to a sterilization range of the endoscope.

In case in which the laser is irradiated through the linear type diffusion part, the end of the optical fiber 140 may be surface-processed to install an optical lens on the end and thereby to straighten out the light transmission.

In case of the lateral type diffusion part, the end of the optical fiber 140 may be cut according to an angle of total reflection so that light is transmitted to only the side surface.

In case of the hemispherical type diffusion part, the end and the side surface of the optical fiber 140 may be surface-processed so that light is transmitted to the side surface and a front surface at the same time in the hemispherical shape.

A protection cap 142 is covered on the end of the optical fiber 140 to protect the end of the processed optical fiber. The protection cap 142 may be made of transparent plastic, transparent acrylic, glass, quartz, PDMS, PTFE, and the like.

The protection cap 142 disposed on the end of the optical fiber 140 has a length of about 5 mm to about 50 mm according to a length of the laser irradiation portion and an outer diameter of about 1 mm to about 5 mm.

When the UV rays and the IR rays are transmitted through the optical fiber 140, light transmissibility of the protection cap 142 is maintained to about 30% to 95%.

To disinfect and sterilize the internal channel surface of the endoscope, the UV rays transmitted to from the optical fiber to the internal channel surface has a light output of about 10 mW to about 10 W and a light density of about 0.005 W/cm$^2$ to about 100 W/cm$^2$.

To dry the internal channel surface of the endoscope at a low temperature, the UV rays transmitted from the optical fiber to the internal channel surface has a light output of about 100 mW to about 30 W and a light density of about 0.005 W/cm$^2$ to about 300 W/cm$^2$.

The porous catheter 160 transfers the optical fiber 140 and the sterilant to the internal channel of the endoscope.

The injection tubing 170 transfers the sterilant injected from the injection device 190 to the porous catheter 160, the connection fixing part 180 connects the optical fiber 140 and the injection tubing 170 for the sterilant to the porous catheter 160, and the injection device 190 adjusts the injection of the sterilant.

The sterilant is injected into the injection tubing 170 through the injection device 190 and then injected into the porous catheter 160. Here, the sterilant is adjusted at a flow rate of about 0.1 ml/min to about 50 ml/min according to a size of the endoscope.

The usable sterilant includes glutaraldehyde, ortho-phthalaldehyde, peracetic acid, hydrogen peroxide, peracetic acid, hydrogen Peroxide, and the like.

As described above, to transfer the optical fiber 140 and the sterilant into the channel of the endoscope, the porous catheter 160 is used.

A main channel of the porous catheter 160 is used for transfer the optical fiber 140 and has a diameter of about 0.5 mm to about 5 mm according to the size of the optical fiber.

An auxiliary channel of the porous catheter 160 is used for injecting the sterilant and has various configurations (e.g., the number of channels, a shape of the channel, and the like).

The porous catheter 160 is made of polytetrafluoroethylene (PTFE), polyethylene, polyvinyl chloride, nylon 66, 11, 12, urethanes, polypropylene, polycarbonate, ABS, pebax, polyetheretherketone (PEEK), polyethylene terephthalate (PET), or the like.

The centring wire 200 locates the optical fiber 140 at a center of the inside of the endoscope.

When light is irradiated to the internal channel of the endoscope by using the optical fiber 140, the centring wire 200 is installed at a rear portion of the irradiation portion of the end of the optical fiber 140 to locate the optical fiber 140 at the center of the inside of the endoscope as illustrated in FIGS. 3 and 4.

The centring wire 200 comes into contact with the internal channel surface of the endoscope when the laser is irradiated and maintains the position of the optical fiber 140 at the center of the inside of the endoscope.

Three or more centring wires 200 may be provided according to the size of the inner diameter of the endoscope.

The centring wire 200 is made of a shape-memory material that is deformable. For example, the centring wire 200 is made of nitinol (nickel and titanium alloy), titanium-palladium-nickel, nickel-titanium-cooper, gold-cadmium, iron-zinc-cooper-aluminum, titanium-niobium-aluminum, uranium-niobium, hafnium-titanium-nickel, iron-manganese-silicon, nickel-titanium, nickel-iron-zinc-aluminum, copper-aluminum-iron, titanium-niobium, zirconium-copper-zinc, nickel-zirconium-titanium, stainless-steel, or the like.

The centring wire 200 may be made of a material selected from materials having a high melting point (about 500° C. or more) and high tensile strength (about 5 ksi or more) to minimize thermal shock. Exemplary examples of the material of the centring wire 200 include steel, silver or gold coating, titanium, tungsten, tungsten-rhenium alloy, superalloy (nickel, cobalt), niobium, tantalum, molybdenum, rhenium, and the like.

To prevent the biofilm from being additionally generated or moved due to the contact between the centring wire 200 and the internal channel surface of the endoscope, the centring wire 200 is disposed at the rear portion of the irradiation portion of the optical fiber 140, and light is irradiated after the centring wire 200 passes along the internal channel of the endoscope.

The centring wire 200 may be disposed at the irradiation portion of the optical fiber 140 at the same time according to a kind of endoscope, and the light may be irradiated at the same time while the centring wire 200 is moved along the internal channel of the endoscope.

The centring wire 200 has a circular or rectangular cross-section and a thickness of about 0.05 mm to about 2 mm.

The centring wire 200 has an installed length of about 0.5 cm to about 5 cm and an expanded diameter of about 1 mm to about 15 mm according to the inner diameter of the endoscope.

Figure 4A:
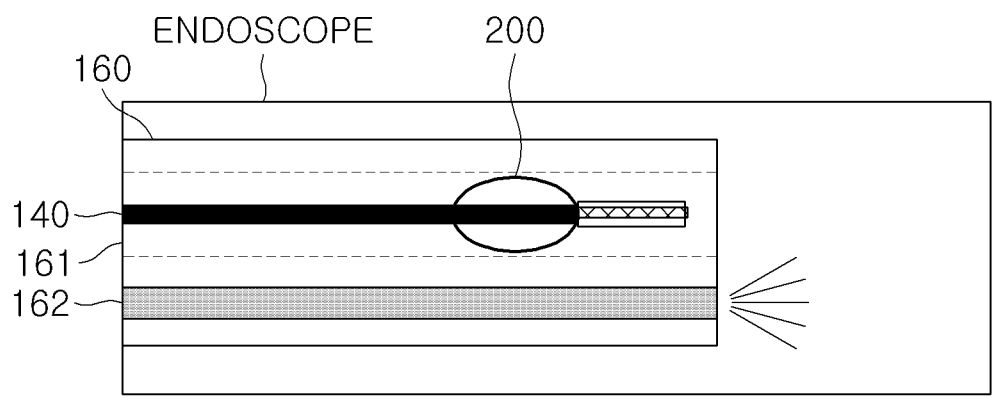
FIG. 4A is a view illustrating a state in which an optical fiber is disposed in an optical fiber channel of a porous catheter.
Figure 4B:
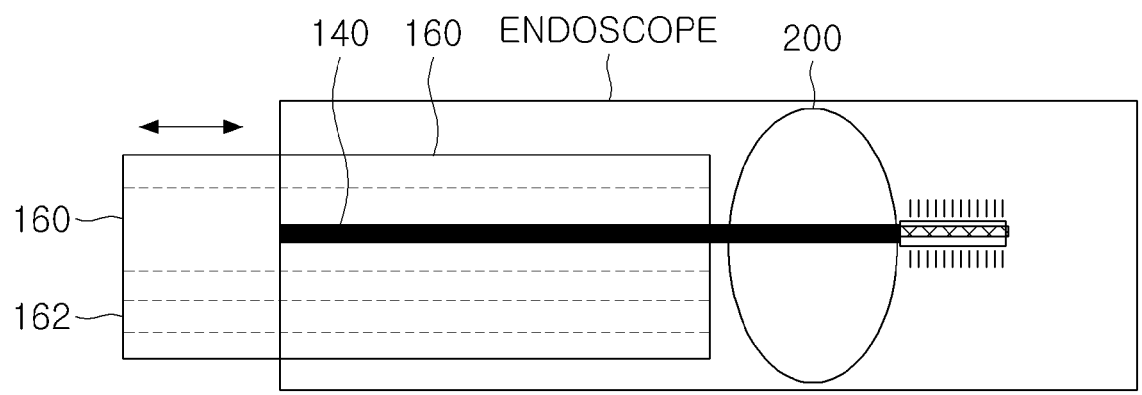
FIG. 4B is a view illustrating an optical fiber discharged from the optical fiber channel of the porous catheter into the endoscope.

As described above, to sterilize and remove the biofilm generated on the internal channel surface of the endoscope, the sterilant is used, and also, to transmit the UV and IR energy, the optical fiber 140 disposed in the optical fiber chamber 161 as illustrated in FIG. 4A is pushed forward from the porous catheter 160 as illustrated in FIG. 4B and then is disposed at the center of the internal channel of the endoscope by using the centring wire 200. The reference numeral 162 represents a sterilant channel.

Figure 5A:
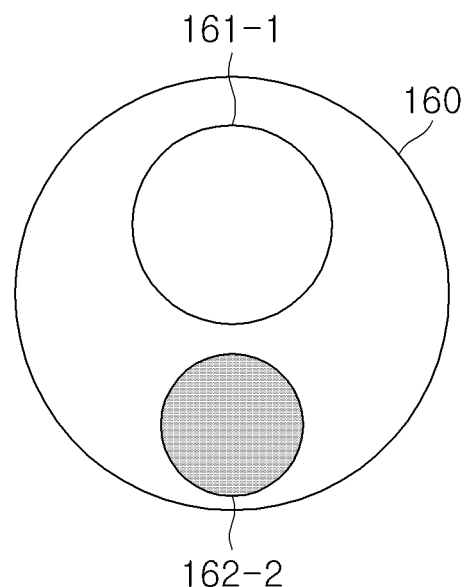
FIGS. 5A and 5B are cross-sectional views of the porous catheter including the optical fiber channel and a sterilant channel.
Figure 5B:
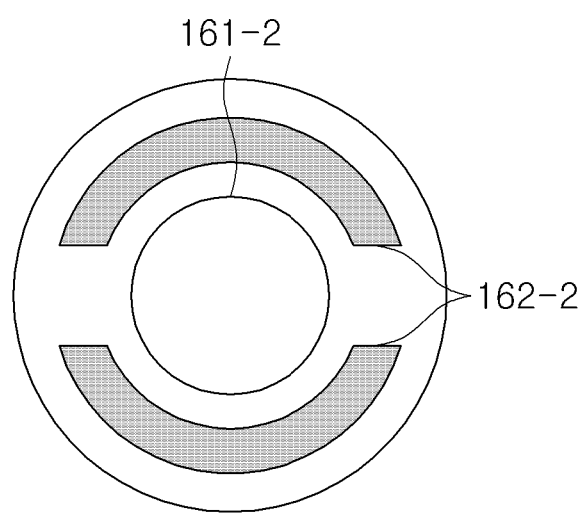

In FIGS. 5A and 5B, two channels provided in the porous catheter 160 are illustrated. The two channels include optical fiber channels 161-1 and 161-2 and sterilant channels 162-1 and 162-2.

As illustrated in FIG. 5A, each of the optical fiber channels 161-1 and 161-2 and the sterilant channels 162-1 and 162-2 has a circular cross-section. The optical fiber channels 161-1 and 161-2 and the sterilant channels 162-1 and 162-2 are installed in parallel to each other, and the optical fiber channel 161-1 has a diameter greater than that of the sterilant channel 162-1.

On the other hand, as illustrated in FIG. 5B, the optical fiber channel 161-2 is disposed at a center of the porous catheter 160, and the sterilant channel 162-2 is installed in a separated half-moon shape around the optical fiber channel 161-2.

After the UV and IR energy is set according to the inner diameter of the endoscope and the thickness of the biofilm, as illustrated in FIG. 6, the optical fiber 140 is pulled back at a predetermined speed.

Figure 6A:
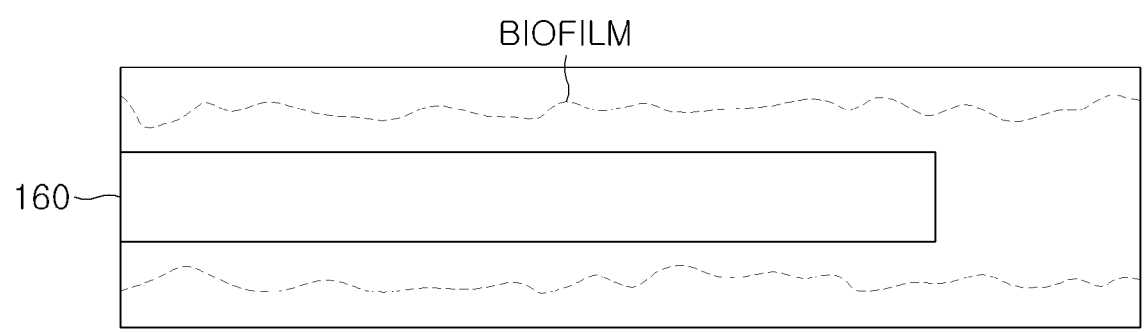
FIG. 6A is a view illustrating the inside of the endoscope before a biofilm is removed.
Figure 6B:
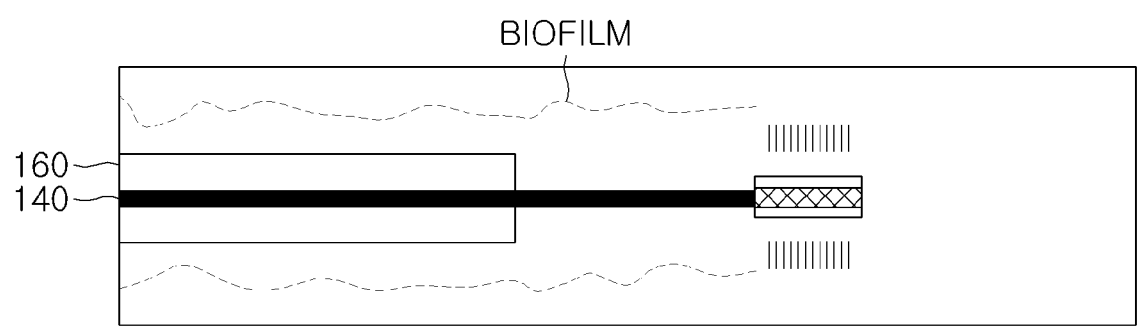
FIG. 6B is a view illustrating the inside of the endoscope while the biofilm is removed.

FIG. 6A illustrates a state in which the biofilm is not removed, and FIG. 6B illustrates a state in which the biofilm is removed.

Here, an order of the method for sterilizing and removing the biofilm is adequately performed according to the inner diameter of the endoscope and the thickness of the biofilm.

FIG. 7 is a flowchart of a method for sterilizing an internal channel surface of an endoscope according to an embodiment of the present invention.

Referring to FIG. 7, in a method for sterilizing an internal channel surface of an endoscope according to an embodiment of the present invention, an inner diameter of the endoscope is checked (S100), and a porous catheter that is adequate for a size of the checked inner diameter of the endoscope is inserted into the endoscope (S110).

Thereafter, a sterilant is injected into the endoscope via an injection tubing and the porous catheter by using an injection device (S120).

Then, a diameter of an optical fiber is set according to a diameter of the catheter inserted into the endoscope (S130), and the optical fiber that is adequate therefor is inserted into the porous catheter (S140).

Thereafter, a pull-back speed of the optical fiber and intensities of UV and IR rays are set (S150).

As described above, the optical fiber provided in a pull-back driver has a pull-back speed of about 0.5 mm/s to about 30 mm/s according to whether the sterilant is used together and a thickness of a biofilm.

In the above-described configuration, an UV light source uses a wavelength of 390 nm to 490 nm and has a light output range of 10 mW to 5 W.

Also, an IR light source 120 uses a frequency of 700 nm to 2,000 nm and has an output range of 10 mW to 10 W.

Then, when the optical fiber is inserted into the endoscope via the porous catheter, the UV and IR rays are irradiated (S160).

Sequentially, in the state in which the UV and IR rays are irradiated into the endoscope, the optical fiber is pulled back through the pull-back driver (S170).

When the biofilm within the endoscope is removed through the pull-back of the optical fiber, the UV light source and the IR light source are turned off so that the UV and IR rays are not irradiated anymore (S180).

Thereafter, the optical fiber is removed from the catheter (S190), and the catheter is removed from the endoscope (S200).

According to the present invention, it may be expected to prevent the infections that may occur due to the frequent use of the endoscope and the low level of the disinfection/sterilization because the endoscopic diagnosis of the patients is done regularly.

According to the present invention, the spreading of pathogens between the patients and the infection of the endoscopists may be prevented due to the disinfection of the endoscope.

According to the present invention, the small amount of sterilant may be used to prevent environment pollution from occurring while the low level of the endoscope disinfection/sterilization is improved to the high level by using the electromagnetic energy.

According to the present invention, it may be possible (reduction of the disinfection time and costs) to be used together with the existing disinfectants through the price competitiveness in the primary/secondary hospitals which are difficult to purchase expensive disinfection systems.

According to the present invention, it may be expected that the effect of improving the sterilization power inside the endoscope is very great in aspects of health and welfare such as the prevention of the secondary infection as well as the economic effect.

According to the present invention, it may be expected to expand the technology base by confirming whether to be applied to various endoscope disinfection through development of the base technologies.

Although preferred embodiments of the present invention have been described for illustrative purposes, those skilled in the art will appreciate that various modifications, additions and substitutions are possible, without departing from the scope and spirit of the invention as disclosed in the accompanying claims. Therefore, the embodiments of the present invention are disclosed only for illustrative purposes and should not be construed as limiting the present invention.

What is claimed is:

1. An apparatus for sterilizing an internal channel surface of an endoscope, the apparatus comprising:
    an ultraviolet light source configured to irradiate ultraviolet rays;
    an infrared light source configured to irradiate infrared rays;
    a porous catheter configured to be inserted into the endoscope;
    a pull-back driver configured to move an optical fiber forward and backward;
    the optical fiber passing through the pull-back driver and disposed in the porous catheter to irradiate the ultraviolet rays and the infrared rays to a surface of the inside of the endoscope;
    a coupling part configured to couple the ultraviolet rays and the infrared rays to output the coupled rays having wavelengths of the ultraviolet rays and the infrared rays to the optical fiber; and
    an injection tubing coupled to the porous catheter and configured to transfer a sterilant to the porous catheter.

2. The apparatus of claim 1, wherein the ultraviolet light source uses a wavelength of about 390 nm to about 490 urn and has a light output range of about 10 mW to about 5 W.

3. The apparatus of claim 1, wherein the ultraviolet light source comprises one of a diode laser, a frequency multiplied solid state laser, an UV flash lamp, and a light emitting diode (LED).

4. The apparatus of claim 1, wherein the infrared light source uses a frequency of about 700 nm to about 2,000 nm and has a light output range of about 10 mW to about 10 W.

5. The apparatus of claim 1, wherein the infrared light source comprises one of a diode laser, a frequency multiplied solid state laser, an IR flash lamp, a light emitting diode (LED), and an infrared bulb.

6. The apparatus of claim 1, further comprising a centring wire disposed at an irradiation portion of an end of the optical fiber to locate the optical fiber at a center of the endoscope.

7. The apparatus of claim 6, wherein the centring wire is made of a shape-memory material.

8. The apparatus of claim 1, wherein the porous catheter comprises an optical fiber channel and a sterilant channel therein, and
    each of the optical fiber channel and the sterilant channel has a circular cross-section, the optical fiber channel and the sterilant channel are installed in parallel to each other, and the optical fiber channel has a diameter greater than that of the sterilant channel.

9. The apparatus of claim 1, wherein the porous catheter comprises an optical fiber channel and a sterilant channel therein, and
    the optical fiber channel has a circular cross-section, and the sterilant channel is disposed in a separated half-moon shape around the optical fiber channel.

10. The apparatus of claim 1, wherein an end of the optical fiber comprises one of a cylindrical type diffusion part, a linear type diffusion part, a lateral type diffusion part, a hemispherical type diffusion part, or a partial cylindrical type diffusion part.

11. The apparatus of claim 1, further comprising a protection cap disposed on an end of the optical fiber to protect the end of the optical fiber.

12. An apparatus for sterilizing an internal channel surface of an endoscope, the apparatus comprising:
    an ultraviolet light source configured to irradiate ultraviolet rays;
    an infrared light source configured to irradiate infrared rays;
    a porous catheter configured to be inserted into the endoscope;
    a pull-back driver configured to move an optical fiber forward and backward;
    the optical fiber passing through the pull-back driver and disposed in the porous catheter to irradiate the ultraviolet rays and the infrared rays to a surface of the inside of the endoscope;
    a coupling part configured to couple the ultraviolet rays and the infrared rays to output the coupled rays to the optical fiber; and
    an injection tubing coupled to the porous catheter and configured to transfer a sterilant to the porous catheter.

* * * * *